(12) United States Patent
Bollini

(10) Patent No.: US 7,005,111 B2
(45) Date of Patent: Feb. 28, 2006

(54) ULTRAVIOLET STERILIZATION APPARATUS

(75) Inventor: Susanna Bollini, Milan (IT)

(73) Assignee: Air Blue S.R.L., Salerno (IT)

( * ) Notice: Subject to any disclaimer, the term of this patent is extended or adjusted under 35 U.S.C. 154(b) by 724 days.

(21) Appl. No.: 09/998,762

(22) Filed: Nov. 28, 2001

(65) Prior Publication Data

US 2002/0098127 A1    Jul. 25, 2002

(30) Foreign Application Priority Data

Nov. 28, 2000  (WO) .................. PCT/EP00/11880

(51) Int. Cl.
 *A62B 7/08* (2006.01)
(52) U.S. Cl. .................. 422/121; 96/223; 96/224; 250/455.11; 422/120; 422/186.3
(58) Field of Classification Search ................ 422/120, 422/122, 124, 105; 96/223, 224
See application file for complete search history.

(56) References Cited

U.S. PATENT DOCUMENTS

| 4,210,429 A | 7/1980 | Golsstein |
| 5,225,167 A | 7/1993 | Wetzel |
| 5,523,057 A * | 6/1996 | Mazzilli ............ 422/121 |
| 5,656,242 A * | 8/1997 | Morrow et al. ............ 96/224 |
| 5,891,399 A * | 4/1999 | Owesen ............ 422/121 |
| 5,894,130 A | 4/1999 | Bach |
| 5,997,619 A | 12/1999 | Knuth et al. |
| 6,497,840 B1 * | 12/2002 | Palestro et al. ............ 422/24 |
| 6,500,387 B1 * | 12/2002 | Bigelow ............ 422/24 |

FOREIGN PATENT DOCUMENTS

| DE | 19652688 A1 | 6/1998 |
| EP | 0 461 310 A1 | 12/1991 |
| GB | 2215234 A | 9/1989 |

OTHER PUBLICATIONS

PCT International Search Report for PCT/EP00/11880, dated Aug. 1, 2001.

* cited by examiner

Primary Examiner—Krisanne Jastrzab
(74) Attorney, Agent, or Firm—RatnerPrestia

(57) ABSTRACT

An ultraviolet sterilization apparatus comprising a housing and a replaceable lamp cartridge package. The lamp cartridge package is a disposable component comprising at least one ultraviolet lamp and an envelope for housing the at least one ultraviolet lamp, the envelope comprising a jacket with a reflective inner surface, an envelop air inlet opening and an envelop air outlet opening, and at least one air-transmitting, ultraviolet-stopping device adjacent at least one of the two envelope openings. The housing has an opening for the inlet of an air flow to be sterilized and an opening for the outlet of a sterilized air flow, said air flow being generated by a fan inside the housing.

12 Claims, 3 Drawing Sheets

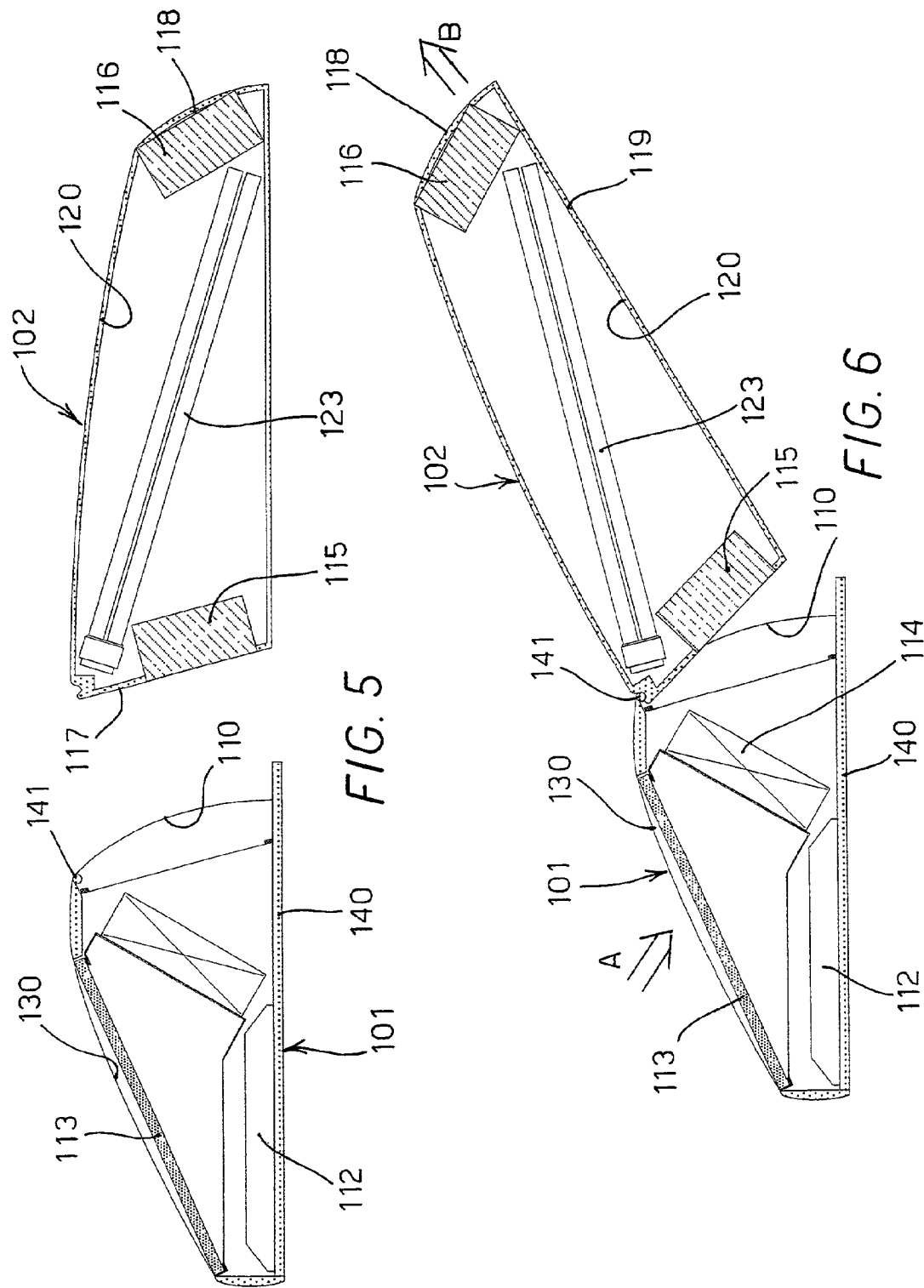

ULTRAVIOLET STERILIZATION APPARATUS

BACKGROUND OF THE INVENTION

The present invention relates to an apparatus for sterilizing the air of rooms and the like by means of ultraviolet radiation, and more particularly to an improved ultraviolet sterilization apparatus.

The sterilizing and bactericide action of ultraviolet radiation known as UV-C (short waves) having a wavelength between 100 and 280 nanometers is used not only for the disinfection of public and private premises, particularly hospitals and nursing homes, but even in rooms opened to the public and also in homes for hygienic and prevention purposes.

There are known devices providing for the use of low pressure mercury vapor lamps as sources of the ultraviolet radiation, which are directed upward but laterally shielded since the direct exposition to this particular radiation is harmful to the persons.

The need to control the bacterial contamination of the air has largely increased in the last years, particularly whereas this parameter can be critical, to comply to safety norms and also for the increased interest for this factor in risk areas where it can relate to the health of the people or the product shelf life.

Beside the evolution and the diffusion of fixed systems of air control in closed environments (laminar flows, negative/positive pressure rooms, high number of air exchanges per hour, absolute filters, etc.) is increasing the demand for stand alone apparatuses that can replace the centralized systems in those cases where these latter cannot be employed for their high costs of installation and management, for the arisen necessity to rapidly sterilize an environment without requiring building works and structural changes or simply because the need is restricted to some areas and it would not be economically convenient to intervene on the whole system.

Moreover movable or easily replaceable apparatuses are better fit to temporary situations such as, for instance, rooms to be restructured or for a temporarily limited need such as in presence of an infectious patient in Dialysis or Intensive care or even for the domiciliary care of immunocompromised patients, in a medical ward, in dentist's surgery, etc.

In this context there are known stand alone apparatuses that use different means to control some parameters of the environmental air: electrostatic filters for reducing the number of suspended particles (smoke and dusts), activated charcoal filters for reducing gases and unpleasant odors, absolute filters (HEPA or ULPA) or germicides ultraviolet radiation (UV-C) to reduce the bacterial charge of the air.

To avoid the side effects of the direct UV-C radiation on human beings it is often convenient to treat the air in a radiation chamber located inside the apparatus where germicidal tubes are housed and the radiation can be kept under control, forcing the room air to pass through the apparatus in the radiation chamber by means of fans and the like.

However the germicidal tubes require frequent servicing because they are negatively effected by the dust that accumulates on their surface and also because their efficiency decays with the time. The use beyond their useful life must be avoided to guarantee an efficient sterilizing action.

Dust also strongly reduces the reflecting properties of the inner walls of the radiation chamber in which the tubes are located with a consequent reduction of the apparatus efficiency.

Proper precautions must also be taken when handling and replacing the tubes since the presence of sebum, dirt and fingerprints on the tube surfaces is another frequent cause of efficiency reduction.

From U.S. Pat. No. 5,894,130 that is hereby incorporated for reference and further details on the sterilizing effects of UV radiation, it is known an ultraviolet sterilization unit having a housing attached to an air heating and cooling system and including two openings into which lamp cartridges are inserted. The lamp cartridge carries ultraviolet lamps operating at a frequency capable of sterilizing air within the system. The cartridges are configured to automatically de-energize the lamps when a lamp cartridge is removed from the housing. When the sterilization unit is a multiple lamp system, upon removal of one of the lamp cartridge is removed all lamps are de-energized, with the de-energizing of the lamps occurring before a user will view the lamp. The disclosed system is applicable to sterilization units which are inserted within the air ducts of forced air heating and cooling systems.

It is therefore desirable a system that allows to avoid the above discussed risks and disadvantages, and is capable to eliminate the problems associated with the dust and the excessive aging of the tubes, that has means to increase the efficacy of the radiation like UV-C reflectors, ensuring a proper, standardized servicing of the apparatus. According to the invention, this is made possible by the use of packages assembled in advance, that cannot be modified and where the inner components cannot be even touched by the operator and most of all is completely safe, simple and fast to be carried out.

An object of the invention is to realize an apparatus for sterilizing the ambient air in a closed environment that allows a safe use of the UV-C radiation in inhabited areas, allowing to fully exploit the germicidal properties of the device without undesired collateral effect, and restoring the previous characteristics of the apparatus at every servicing by replacing the germicidal tubes and the reflective walls of the radiation chamber, which operation can be precisely scheduled (since according to an advantageous embodiment of the invention, it is the device itself that indicates the right time interval and time expiration) and kept totally safe and carried out directly by the user without requiring skilled technician personnel with consequent advantages in terms of practicality, economy and reduction of the problems of post-sale technical assistance.

SUMMARY OF THE INVENTION

The apparatus of the invention comprises two main components that are detachable from one another: a supporting frame or housing and a replaceable (and disposable) component or cartridge. The housing or supporting frame incorporates means for fixing the apparatus to a wall or to a pedestal, electric connections, a general control circuitry preferably realized with one or more electronic cards, with control and adjustment buttons, switches and indicator lights, at least a fan and a support for a dust filter for removing the coarser particles from the air flow.

The supporting frame further incorporates an arrangement for securing the cartridge, this latter comprising an envelope or housing of plastics, cardboard, wood or any low cost material that is stiff enough, internally covered or lined by a film of reflecting aluminum to increase the efficiency of the UV radiation.

The housing contains at least a germicidal tube and has two openings for the air entry and exit, such openings being provided with means that allow the passage of the air but stops the germicidal radiation, such as for instance a dark filter or an activated charcoal filter, an optic labyrinth, etc. and a plurality of electric contacts for one or more UV lamp disposed inside the housing and also a system (comprising for example a microchip, a magnetized strip and so on) capable of recording and counting the time of use of the apparatus, as well to supply data for identifying the cartridge

BRIEF DESCRIPTION OF THE DRAWINGS

FIGS. 5 and 6 are cross section views illustrating another embodiment of a sterilizing apparatus according to the invention.

DETAILED DESCRIPTION OF PREFERRED EMBODIMENTS

Figure 1:
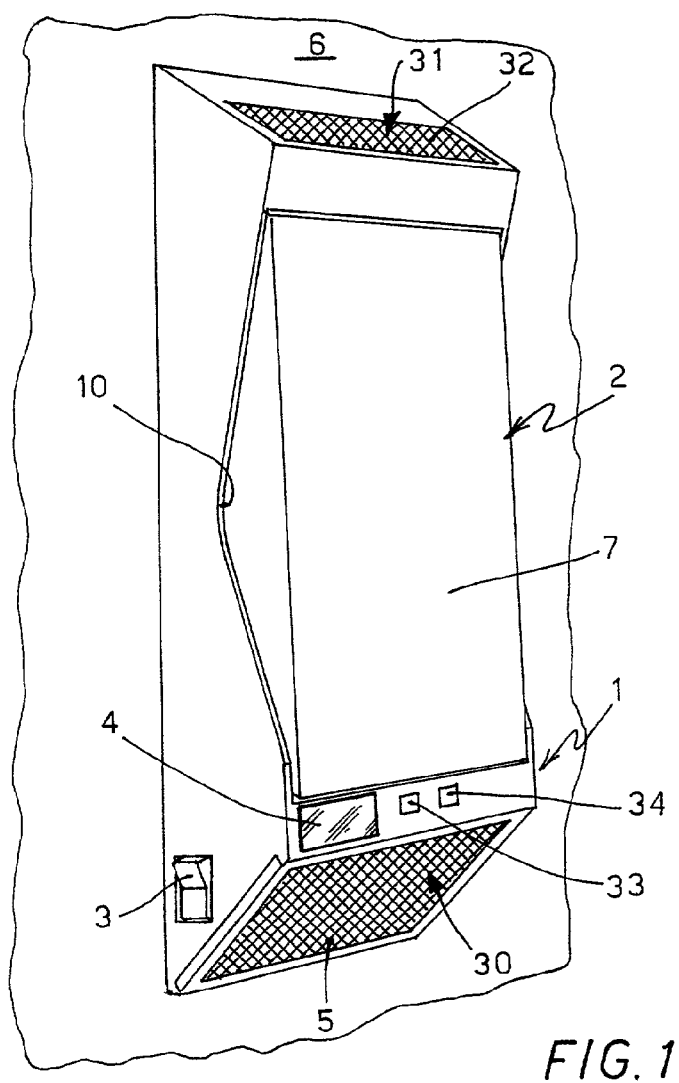
FIG. 1 is a perspective view of a sterilizing apparatus according to the invention.
Figure 2:
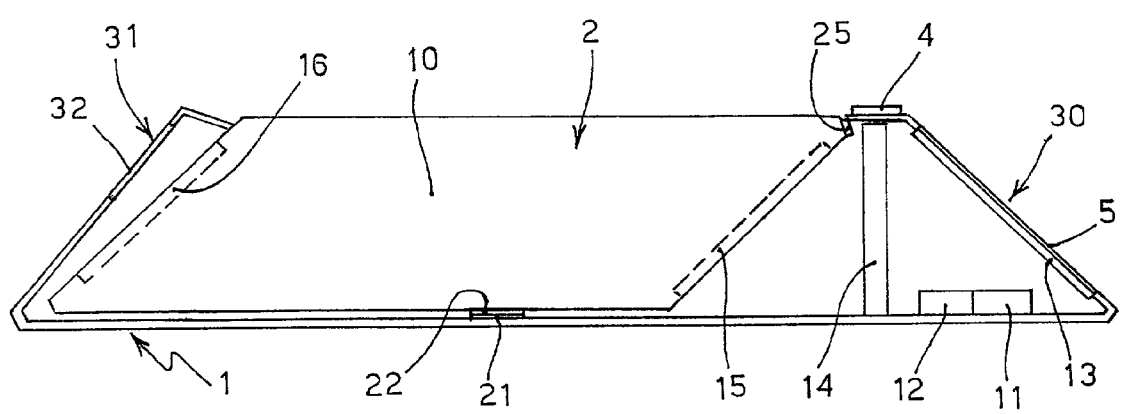
FIG. 2 is longitudinal cross section of the apparatus shown in FIG. 1.

With reference to FIGS. 1 and 2, a sterilization apparatus according to the invention comprises a support frame or housing 1 provided with an aperture 10, and a disposable lamp cartridge 2 at least a portion of which can be inserted into and/or fastened to the housing. For sake of clarity, FIG. 2 does not show details of the cartridge. The support frame 1 which has preferably an elongated shape, is further provided with an inlet opening 30 protected by a grid 5 at one end and an outlet opening 31 at the opposed end, this latter opening being protected by a grid 32 and preferably having a surface smaller than the cross section of the housing so as to increase the speed of the outgoing sterilized air thus preventing air stifling near the outlet opening. As schematically shown in FIG. 2, a chamber or space 35 is provided between the cartridge 2 and the wall of the support frame 1 containing the opening 31 and the grid 32.

The support frame 1 is formed as supporting frame incorporating means (not shown) for fixing the apparatus to a wall 6, and houses a power supply 11 coupled to the mains or other electric source for feeding the whole unit, and a general control circuitry 12 preferably realized with one or more electronic cards. The housing 1 further contains a first coarse filter 13 covering the inlet opening 30 of the housing together with the protection grid 5 through which the air enters the apparatus sucked by one or more (axial) fans 14 located inside the housing and interposed between such filter 13 and the aperture 10. The coarse filter 13 is mainly provided for preventing dust particles from entering the apparatus.

The support frame or housing 1 further incorporates control and adjustment buttons, such as a ON/OFF switch 3, a display 4 and indicator lights such as 33 and 34, and an arrangement for securing the cartridge 2 to the housing as will be illustrated in detail later. In the illustrated embodiment the switch 3 is located on a side of the housing and the display 4 is positioned on a narrow wall of the housing adjacent the cartridge and carrying electrical connections 25 as well as blocking means on the surface facing the inside space of the housing. Advantageously the display shows the operating hours of a cartridge, i.e. the time for which the lamps in the presently inserted cartridge has been operated, so that the operator can immediately realize when a cartridge has to be replaced.

Advantageously the flat panel 7 forming the visible surface of the cartridge 2 when this latter is fitted within the housing 1, is adapted to carry an advertising message and the like, e.g. by applying an adhesive sheet over its surface.

Figure 3:
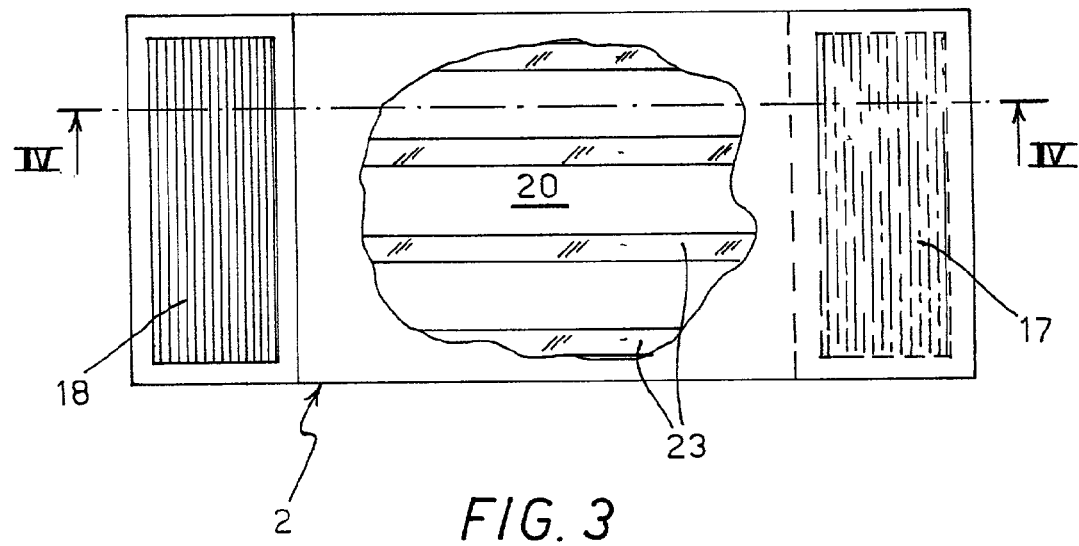
FIG. 3 is a top view of the replaceable lamp cartridge of the apparatus shown in FIGS. 1 and 2.
Figure 4:
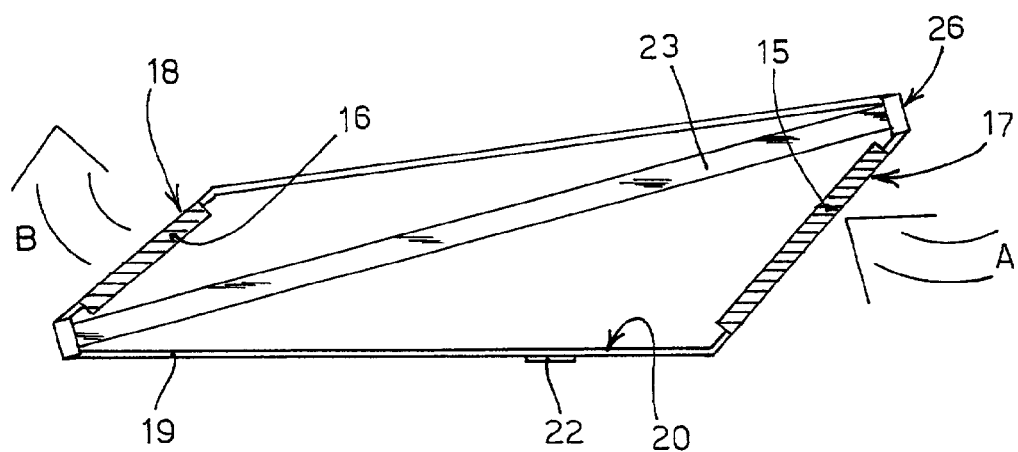
FIG. 4 is a cross section view along the line IV—IV of FIG. 3, illustrating further details of the replacement cartridge.

With reference to FIGS. 3 and 4, the lamp cartridge 2 comprises an envelope 19 made of a low-cost relatively-stiff material such as plastics, cardboard, wood or the like, having a reflective inner surface 20 to increase the sterilizing efficiency of the UV radiation. According to a presently preferred embodiment, such envelope is internally lined or coated by a film of reflecting material such as aluminum.

The cartridge 2 further contains at least one germicidal tube 23 and has two openings 17, 18 for the entry and exit of an air flow, schematically shown by arrows A and B, respectively. At least one of such openings is provided with means that allow the passage of the air but stops the germicidal radiation, such as for instance a dark filter or an activated charcoal filter and similar devices. In the illustrated embodiment, the replaceable cartridge 2 provides for two UV stopping devices or filters 15, 16 one at each end of the cartridge, which filters are discarded together with the cartridge when this latter is replaced.

Advantageously, as shown in the figures, the lamp or each lamp is a tube of the type provided with contacts 26 at one end only and is diagonally positioned inside the envelope 19 so as to reduce the cartridge size. The contacts 26 are connected to a socket or corresponding contacts 25 formed on the inside of the housing 1, and the arrangement is such that the power supply to the lamp is removed unless the cartridge is properly positioned in the aperture 10.

In accordance with another embodiment of the invention, one or both UV stopping devices 15, 16 can be realized as a durable UV stopping device, such as a so called optic labyrinth, i.e. a meander path adapted to cancel the UV radiation through multiple reflections onto an adsorbing inner surface, or through suitable means, and located within the housing, e.g. on the inside of the grid 5 or 8.

The disposable cartridge 2 further comprises a system (of known type comprising for example a microchip and not shown in the Figures) capable of recording and counting the time of use of the unity, as well to supply data for identifying the cartridge and check its compatibility with the device. Advantageously a magnetized strip 21 is secured to the inner bottom surface of the housing and cooperates with a metal strip 22 on the cartridge surface to secure the coupling between the housing and the cartridge.

According to the embodiment illustrated in FIGS. 5 and 6, the support member 101 is formed with an opening 110, onto which a cantilevered disposable cartridge 102 is applied, said cartridge containing germicidal lamps 123 and being adapted to be secured to one end of the support frame 101.

The frame 101 is formed as a supporting structure provided with a base 140 that incorporates means (shown not) to secure the apparatus to a wall, and provides for an articulated joint 141 into which the cartridge is fitted, such joint allowing a partial rotation of the cartridge. The support member 101 includes a assembly 112 incorporating a power supply to be connected to the electric mains or other source of electric power, and an electronic control circuitry, a first coarse filter or pre-filter 113 that covers the opening 130 of the support member and two helical fans 114 disposed between the filter 113 and the other opening 110 in the support member.

The cartridge 102 is made of a relatively rigid material, such as plastics, cardboard, wood or the like, in case with a reflecting inner surface 120, for instance thanks to a reflecting coating or liner, such as an aluminum film. The cartridge 102 has an elongated shape and comprises a cartridge housing 119 provided with two openings at the ends thereof, respectively an opening 117 for the inlet and an opening 118 for the outlet of a flow of air schematically indicated by the arrows A and B. At least one of the openings 117, 118 is equipped with means 115, 116 allowing the passage of the air flow but stopping the germicidal radiation, such as for example a dark filter or an activated charcoal filter and similar apparatuses. These filters are disposed together with the cartridge when this latter is replaced.

What is claimed is:

1. An ultraviolet sterilization apparatus comprising:
    a lamp cartridge package comprising at least one ultraviolet lamp and an envelope for housing the at least one ultraviolet lamp, the envelope comprising a jacket with a reflective inner surface, an envelope air inlet opening and an envelope air outlet opening, and at least one air-transmitting, ultraviolet-stopping device adjacent at least one of the two envelope openings;
    a housing including an aperture for removably receiving said lamp cartridge package and at least one opening for air to enter or leave the housing;
    the combination of said housing and said lamp cartridge package defining a closed air passageway through said housing and said envelope;
    said housing further including an air propulsion device for generating an air flow and propelling the air flow through said closed passageway.

2. The ultraviolet sterilization apparatus of claim 1, wherein said housing air opening further comprises a coarse dust filter forming a wall of said housing, and wherein said air propulsion device further comprises at least one fan interposed between said coarse dust filter and said lamp cartridge package.

3. The ultraviolet sterilization apparatus of claim 1, wherein said housing further comprises a wall-mounting device for fixing said housing to a wall.

4. The ultraviolet sterilization apparatus of claim 1, wherein the jacket is of a material selected from the group consisting of plastic, cardboard, and wood, and wherein the reflective inner surface of the jacket comprises a reflecting film.

5. The ultraviolet sterilization apparatus of claim 1, wherein the housing further comprises an articulated joint for removably connecting the lamp cartridge package to the housing.

6. The ultraviolet sterilization apparatus of claim 1, wherein the lamp cartridge package further comprises two air-transmitting ultraviolet-stopping devices, wherein each of the air-transmitting ultraviolet-stopping devices is adjacent to one of the two air inlet and outlet openings.

7. The ultraviolet sterilization apparatus of claim 1, said at least one air-transmitting ultraviolet-stopping devices being selected from the group consisting of a dark filter, an activated charcoal filter and an optic labyrinth.

8. The sterilization apparatus of claim 1, wherein the housing further comprises a power supply for powering the ultraviolet sterilization apparatus and control circuitry associated with at least one control and at least one display for controlling and monitoring the operation of said apparatus.

9. The ultraviolet sterilization apparatus of claim 8, wherein the lamp cartridge package further comprises a plurality of electrical contacts, and wherein the housing further comprises an electrical conduit selected from the group consisting of a socket and electrical contacts, for connecting the lamp cartridge package to the power supply of the housing.

10. The ultraviolet sterilization apparatus of claim 1, wherein the housing further comprises a magnetized strip secured to an inner surface of the housing, and wherein the lamp cartridge package further comprises a magnetized strip secured to an outer surface of the lamp cartridge package, said magnetized strips being adapted to assist in retaining said lamp cartridge package in said housing.

11. The ultraviolet sterilization apparatus of claim 1, wherein the ultraviolet lamp is tube-shaped and is positioned diagonally inside the lamp cartridge package.

12. The ultraviolet sterilization apparatus of claim 1, wherein said lamp package includes a flat panel adapted to carry an advertising message and said flat panel is visible when said lamp package is fitted within said housing.

* * * * *